United States Patent
You

(10) Patent No.: US 12,303,229 B2
(45) Date of Patent: May 20, 2025

(54) METHOD FOR TRANSMITTING AND RECEIVING BIOMETRIC INFORMATION WITHOUT LOSS IN CONTINUOUS BLOOD GLUCOSE MONITORING SYSTEM

(71) Applicant: I-SENS, INC., Seoul (KR)

(72) Inventor: Choong Beom You, Seoul (KR)

(73) Assignee: I-SENS, INC., Seoul (KR)

( * ) Notice: Subject to any disclaimer, the term of this patent is extended or adjusted under 35 U.S.C. 154(b) by 645 days.

(21) Appl. No.: 17/627,563

(22) PCT Filed: Mar. 13, 2020

(86) PCT No.: PCT/KR2020/003518
§ 371 (c)(1),
(2) Date: Jan. 14, 2022

(87) PCT Pub. No.: WO2021/015389
PCT Pub. Date: Jan. 28, 2021

(65) Prior Publication Data
US 2022/0257119 A1    Aug. 18, 2022

(30) Foreign Application Priority Data

Jul. 22, 2019   (KR) .......................... 10-2019-0088227

(51) Int. Cl.
*A61B 5/00* (2006.01)
*A61B 5/15* (2006.01)
(Continued)

(52) U.S. Cl.
CPC ...... *A61B 5/0024* (2013.01); *A61B 5/150748* (2013.01); *A61B 5/7221* (2013.01);
(Continued)

(58) Field of Classification Search
None
See application file for complete search history.

(56) References Cited

U.S. PATENT DOCUMENTS

| 9,980,140 B1 | 5/2018 | Spencer et al. |
| 2005/0182306 A1 | 8/2005 | Sloan |

(Continued)

FOREIGN PATENT DOCUMENTS

| JP | 2015-119910 | 7/2015 |
| JP | 2018-42058 | 3/2018 |

(Continued)

OTHER PUBLICATIONS

Examination Report No. 1 dated May 16, 2023 for Australian Patent Application No. 2020317807.

(Continued)

*Primary Examiner* — Jutai Kao
(74) *Attorney, Agent, or Firm* — WOMBLE BOND DICKINSON (US) LLP

(57) ABSTRACT

The present disclosure relates to a method for transmitting or receiving biometric information in a continuous glucose monitoring system and, more specifically, to a method for transmitting or receiving biometric information, in which: when a sensor transmitter generates a transmission packet, the transmission packet is generated to include a generation identifier for identifying the transmission packet or biometric information according to a generation order of the transmission packet or the biometric information, and therefore the biometric information may be transmitted or received without a loss thereof via the generation identifier; and a transmission packet or biometric information, which a communication terminal has failed to receive, is correctly determined on the basis of a packet generation identifier or a total number of transmission packets, so that only biometric information or a transmission packet, which has failed to be received between the sensor transmitter and the communication terminal, may be transmitted or received in a distinguished manner.

4 Claims, 10 Drawing Sheets

(51) Int. Cl.
*H04W 4/38* (2018.01)
*H04L 1/1867* (2023.01)

(52) U.S. Cl.
CPC .......... *H04W 4/38* (2018.02); *A61B 2505/07* (2013.01); *H04L 1/189* (2013.01)

(56) References Cited

U.S. PATENT DOCUMENTS

| | | | |
|---|---|---|---|
| 2010/0265073 A1* | 10/2010 | Harper | H04W 4/80 340/573.1 |
| 2011/0196451 A1 | 8/2011 | Hill | |
| 2013/0208079 A1* | 8/2013 | Yassur | H04N 7/152 348/14.09 |
| 2013/0217346 A1* | 8/2013 | Freeman | H04W 4/70 455/90.1 |
| 2014/0107449 A1 | 4/2014 | Ecoff et al. | |
| 2014/0365694 A1 | 12/2014 | Bolton et al. | |
| 2015/0230085 A1 | 8/2015 | Xue | |
| 2016/0051192 A1 | 2/2016 | Kang et al. | |
| 2020/0085302 A1* | 3/2020 | Kubo | H04W 24/04 |

FOREIGN PATENT DOCUMENTS

| | | |
|---|---|---|
| JP | 2019-510388 | 4/2019 |
| KR | 10-2002-0092420 | 12/2002 |
| KR | 10-2008-0031175 | 4/2008 |
| KR | 10-1169440 | 8/2012 |
| KR | 10-2016-0066532 | 6/2016 |
| KR | 10-2019-0043034 | 4/2019 |
| WO | 2017/105600 | 6/2017 |

OTHER PUBLICATIONS

International Search Report for PCT/KR2020/003518 mailed on Jun. 22, 2020 and its English translation from WIPO (now published as WO 2021/015389).
Written Opinion of the International Searching Authority for PCT/KR2020/003518 mailed on Jun. 22, 2020 and its English translation by Google Translate (now published as WO 2021/015389).
Office Action dated Jan. 10, 2023 for Japanese Patent Application No. 2022-502307 and its English translation from Global Dossier.
Gomez, Carles et al.: "Overview and Evaluation of Bluetooth Low Energy: An Emerging Low-Power Wireless Technology", Aug. 29, 2012, vol. 12, No. 9, pp. 11734-11753, DOI: 10.3390/s120911734.
International Preliminary Report on Patentability (Chapter I) for PCT/KR2020/003518 issued on Jan. 25, 2022 and its English translation from WIPO (now published as WO 2021/015389).
Office Action dated May 10, 2023 for European Patent Application No. 20844655.9.
Office Action dated Jul. 9, 2024 for Japanese Patent Application No. 2023-211419 and its English translation from Global Dossier.
Notice of Allowance dated Jun. 30, 2023 for Japanese Patent Application No. 2022-502307 and its English translation by Google Translate.

* cited by examiner

[Fig. 1]
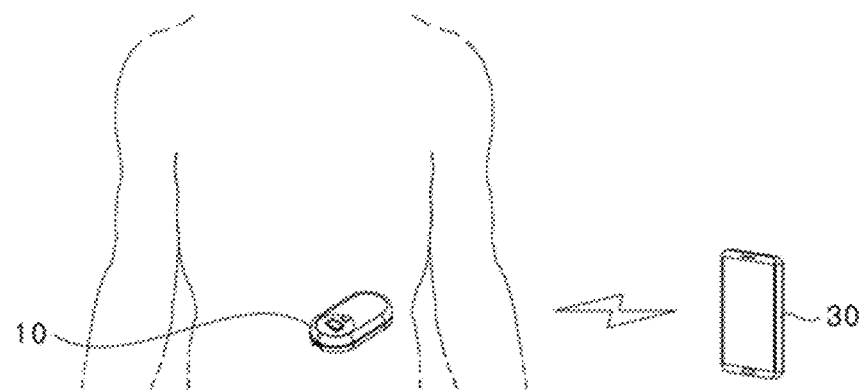
[Fig. 2]
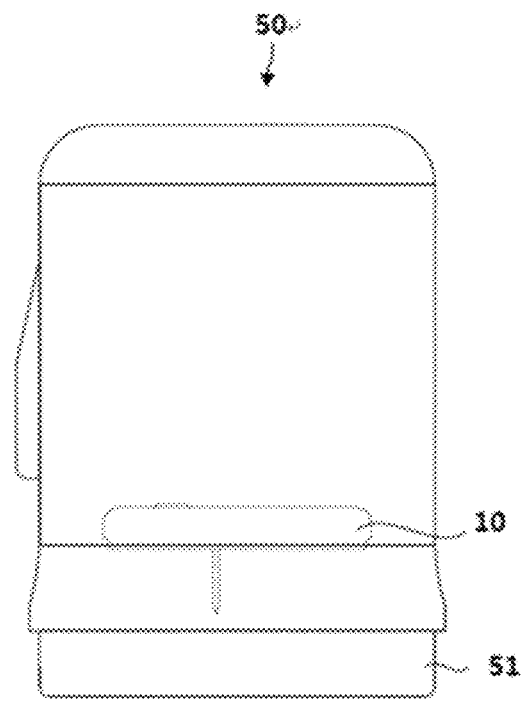

[Fig. 3]
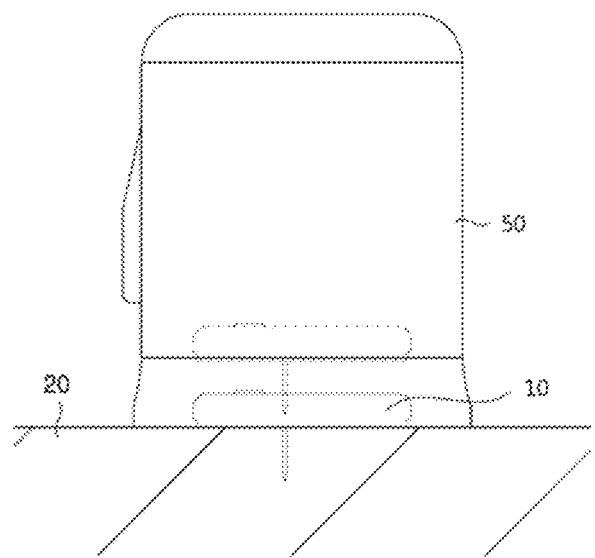
[Fig. 4]
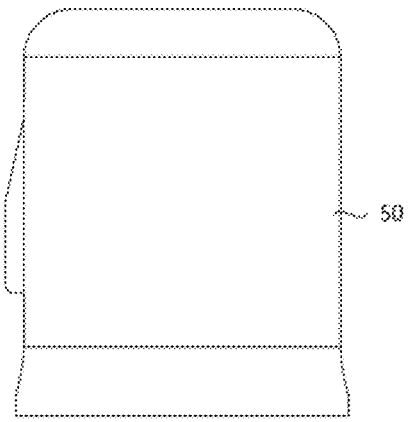
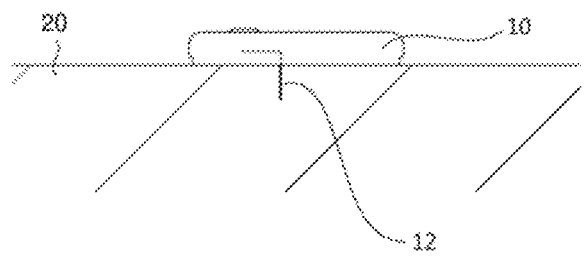

[Fig. 5]
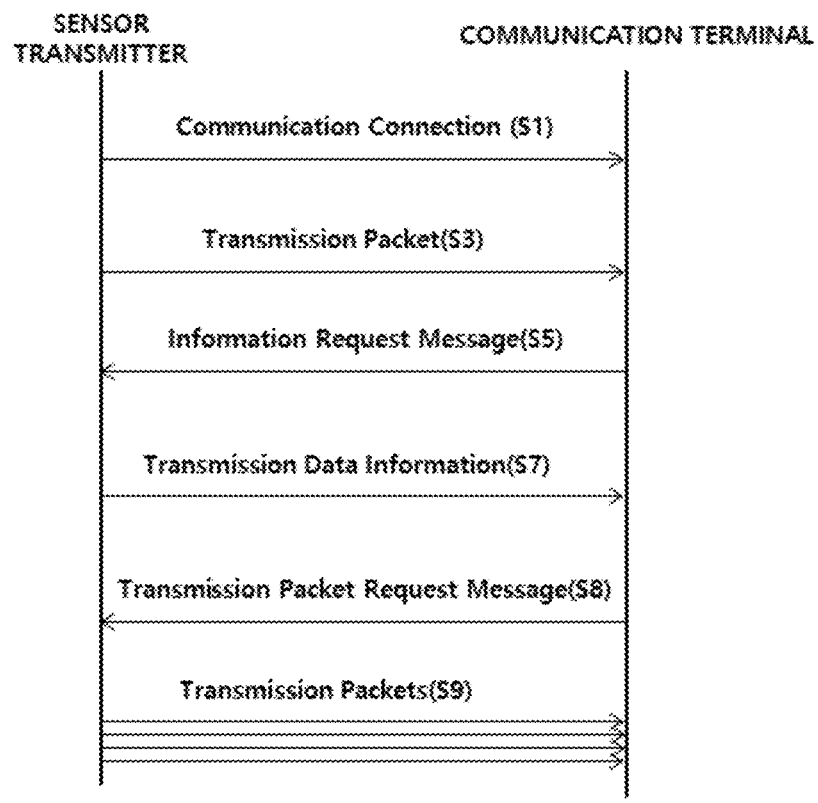
[Fig. 6]
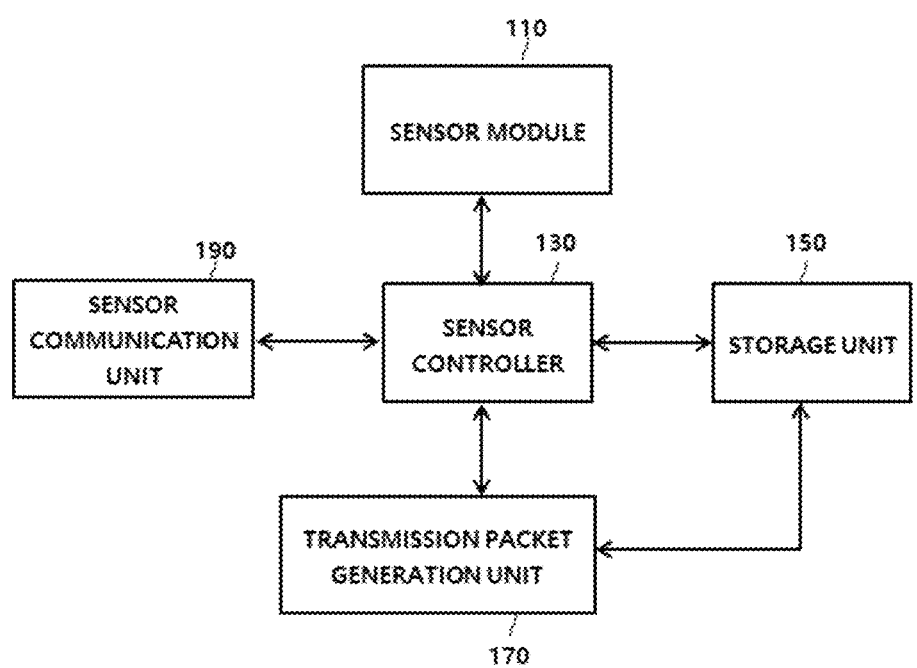

[Fig. 7]
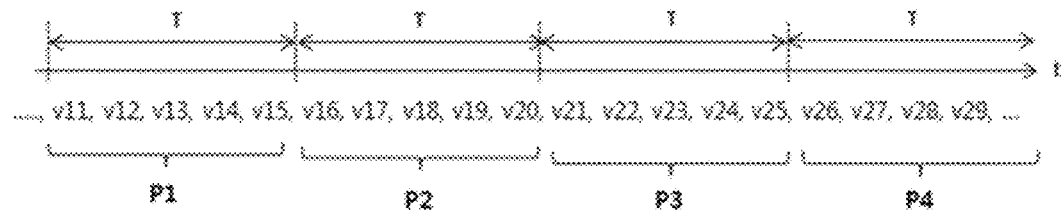
[Fig. 8]
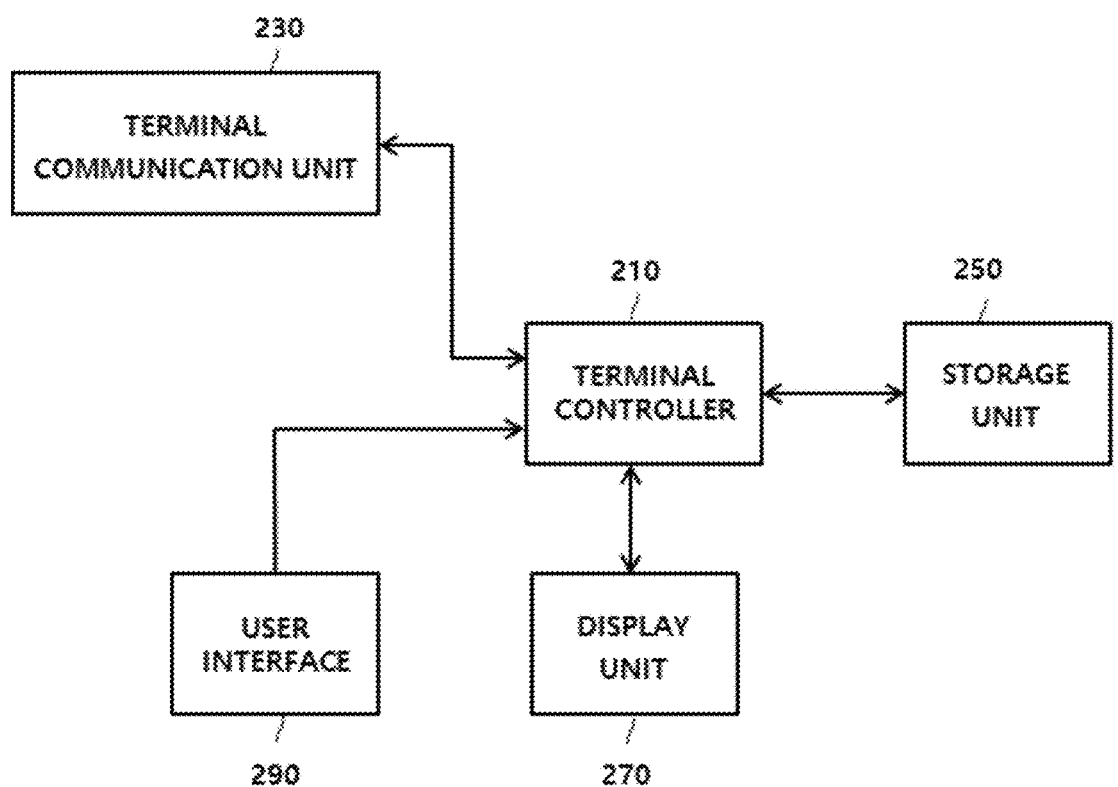

[Fig. 9]
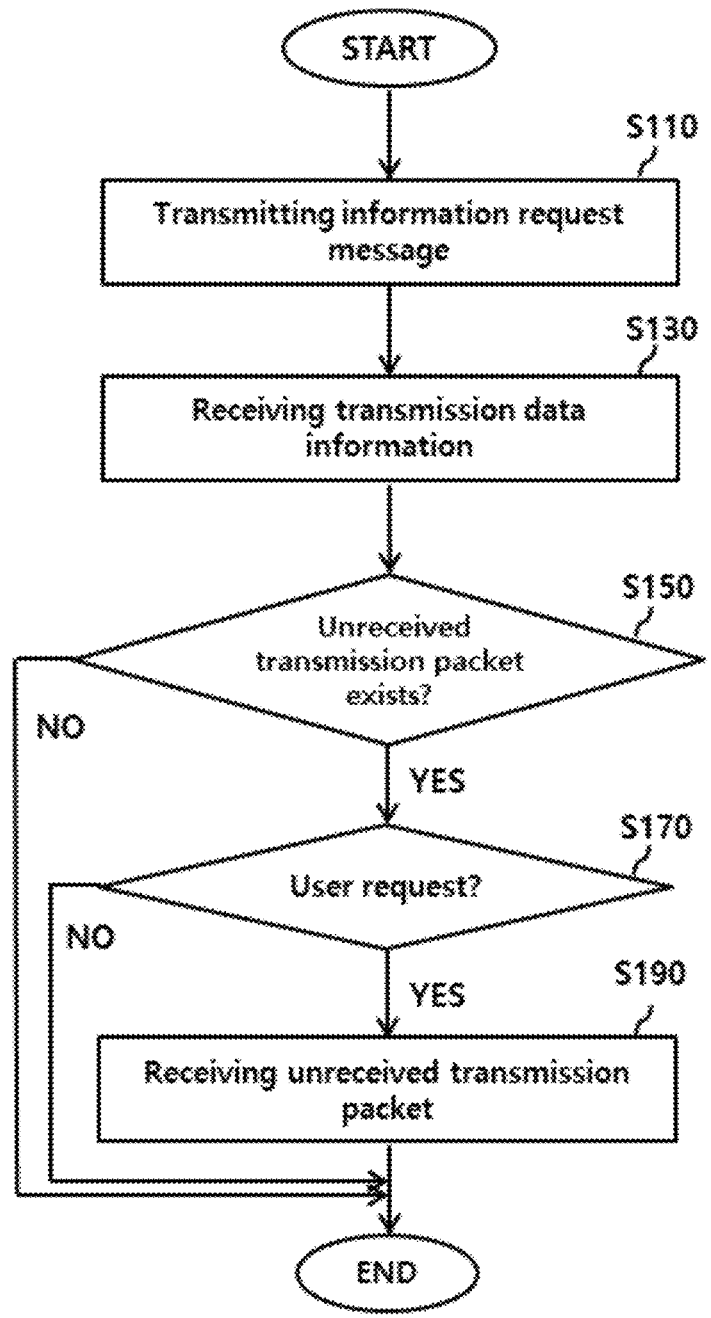

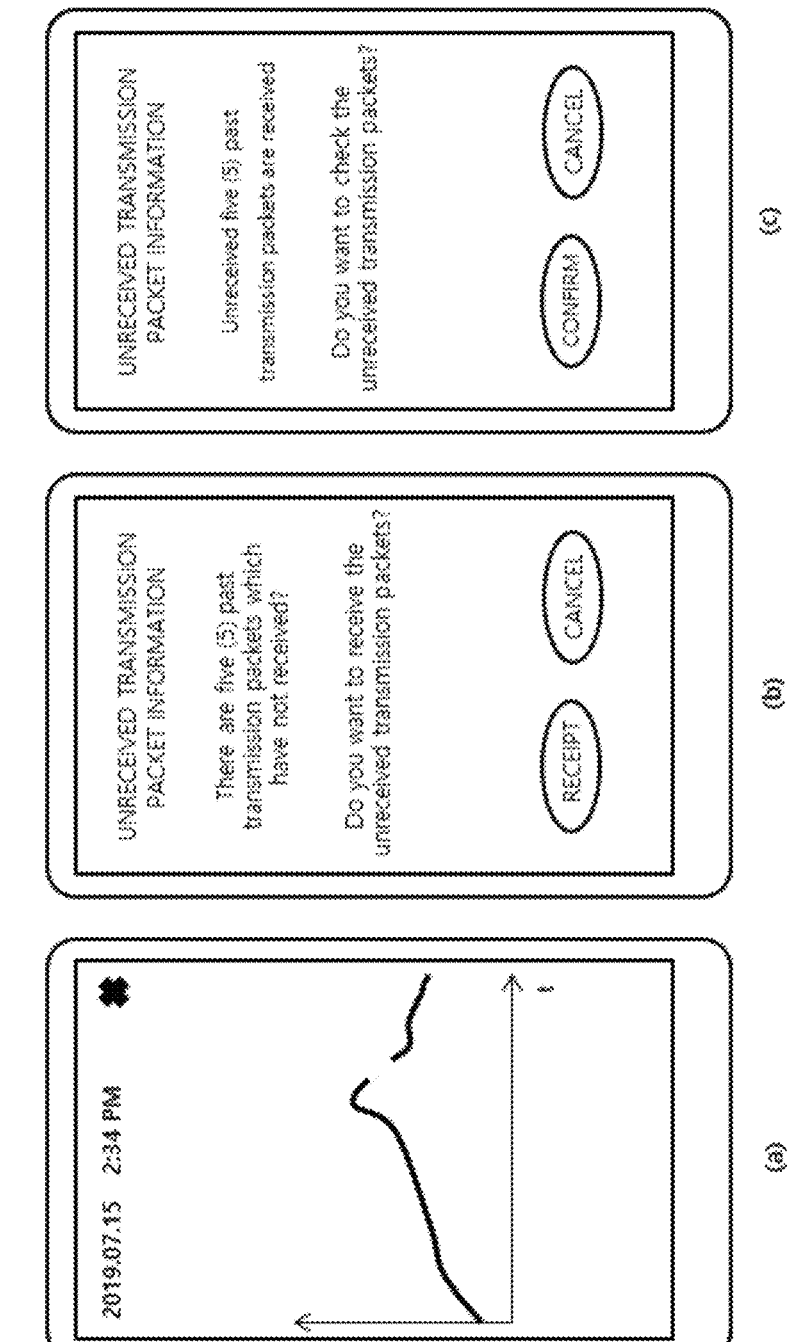
[Fig. 10]

[Fig. 11]
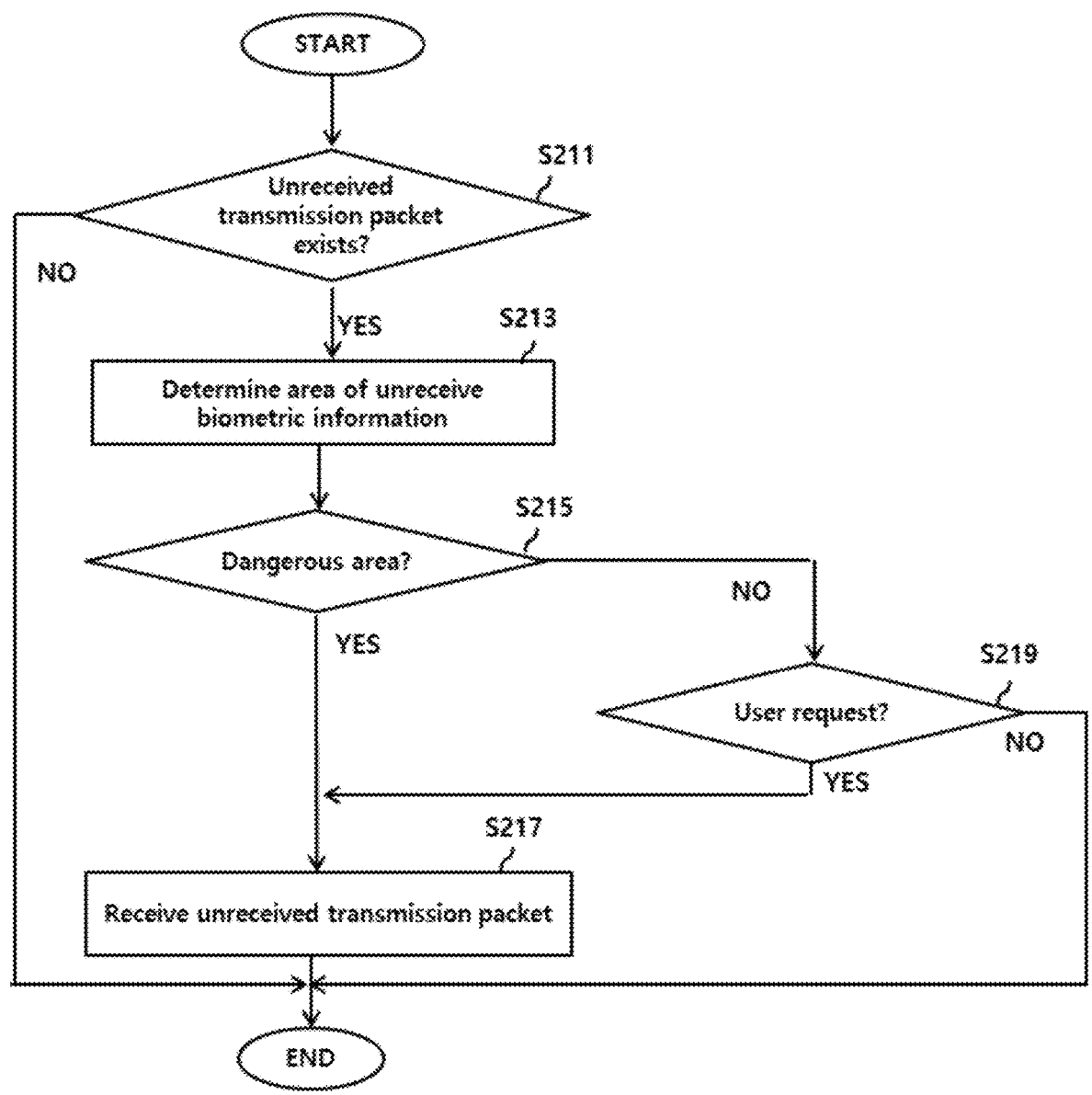

[Fig. 12]
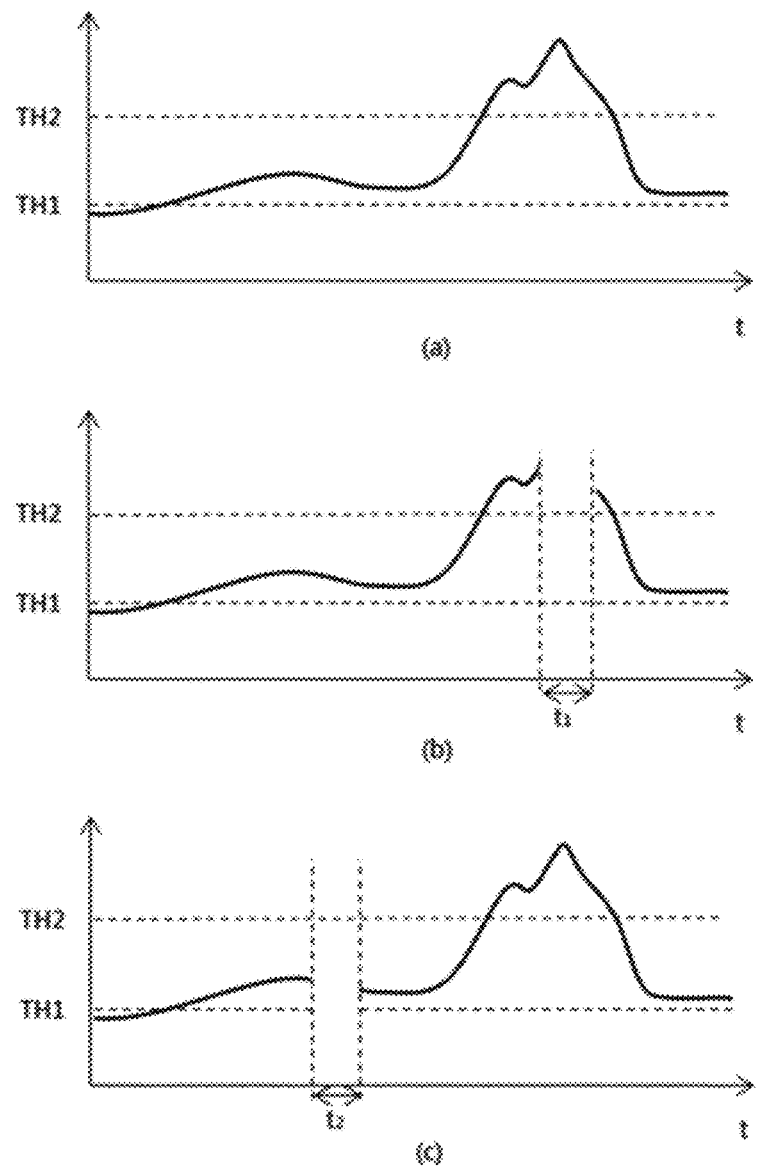

[Fig. 13]
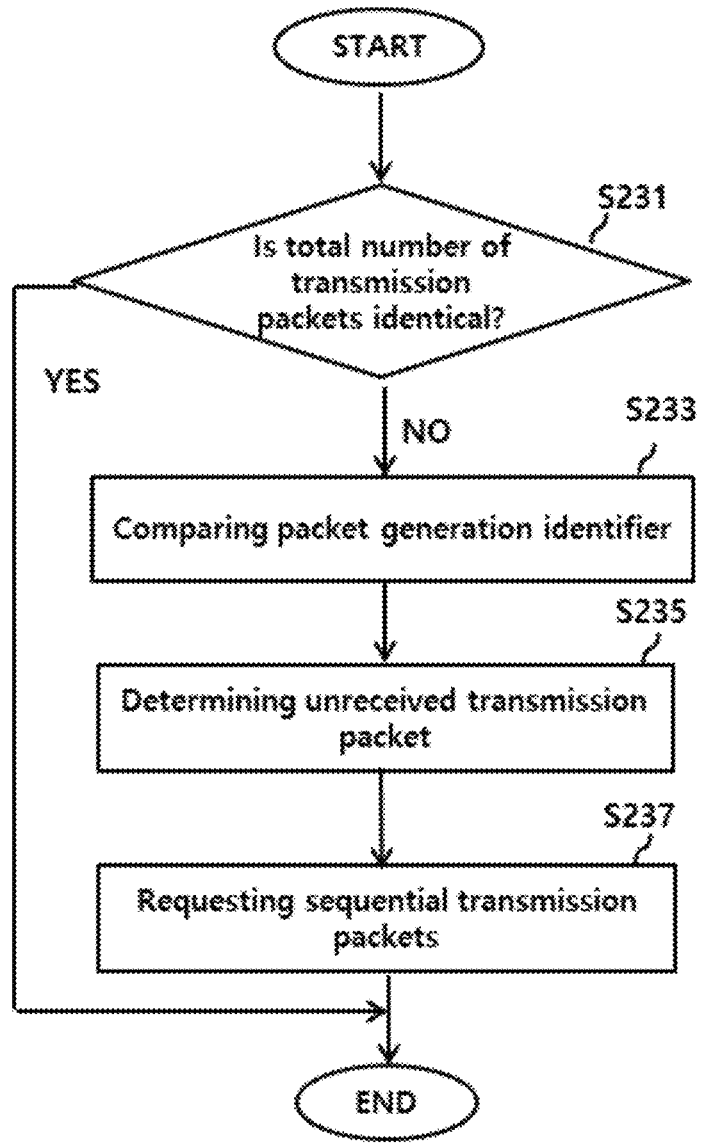

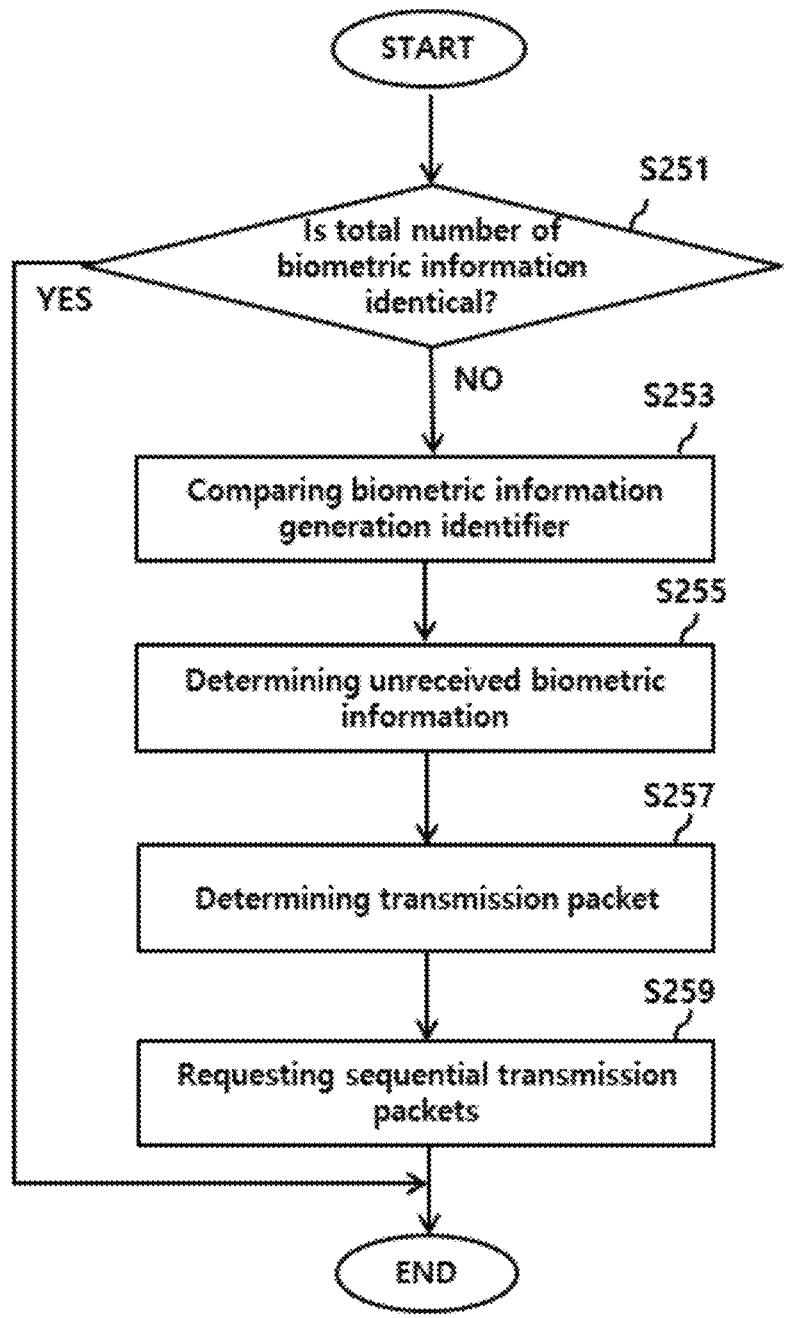
[Fig. 14]

METHOD FOR TRANSMITTING AND RECEIVING BIOMETRIC INFORMATION WITHOUT LOSS IN CONTINUOUS BLOOD GLUCOSE MONITORING SYSTEM

CROSS-REFERENCE TO RELATED APPLICATIONS

The present application is the U.S. National Phase of PCT Application No. PCT/KR2020/003518 filed on Mar. 13, 2020, which claims the priority to Korean Patent Application No. 10-2019-0088227 filed on Jul. 22, 2019, the entire contents of which are incorporated herein by reference.

TECHNICAL FIELD

The present disclosure is generally related to a method for transmitting and receiving biometric information in a continuous blood glucose monitoring system, in more detail, a method for transmitting and receiving biometric information in a continuous blood glucose monitoring system in which, by generating a transmission packet so as to include a generation identifier for identifying biometric information or the transmission packet according to a generation order of the biometric information or the transmission packet when generating the transmission packet, the biometric information can be transmitted and received without loss through the generation identifier, and by precisely determining one or more transmission packets or biometric information not received by a communication terminal based on a packet generation identifier or a total number of transmission packets, only the transmission packets or biometric information not received between a sensor transmitter and the communication terminal can be found and transmitted and received.

BACKGROUND

Diabetes is a chronic medical condition that is common in modern people, and in the Republic of Korea, there are 2 million diabetes patients, about 5% of the total population.

Diabetes occurs when the absolute level of the sugar level in blood is high due to the absolute deficiency or relative insufficiency of insulin, produced by the pancreas, caused by various reasons such as obesity, stress, poor eating habits, and inherited hereditary factors and imbalance regarding glucose in the blood.

The blood usually contains a certain concentration of glucose, and tissue cells gain energy from the glucose.

However, when the glucose is increased excessively more than needed, the glucose cannot be properly stored in the liver, muscle, or adipose tissue and is accumulated in the blood, because of this, patients with diabetes maintain a much higher blood glucose level than normal people, and as excessive blood glucose passes through the tissues and is discharged into the urine, it results in deficiency of glucose, which is absolutely necessary for all tissues of the body, thereby causing abnormalities in respective body tissues.

Diabetes is characterized by substantial absence of subjective symptoms at the beginning of the condition, when diabetes progresses, diabetes-specific symptoms such as overdrink, overeat, polyuria, weight loss, weariness, skin itchiness, and lower ability of naturally healing on injury on hands and feet are shown, and further progression of diabetes leads to complications such as visual disturbances, hypertension, kidney disease, paralysis, periodontal disease, muscle spasms and neuralgia, as well as gangrene.

In order to diagnose diabetes beforehand and manage to prevent the progression of diabetes into complications associated therewith, systematic blood glucose measurement and treatment should be performed.

In order to manage diabetes, the continuous measurement of blood glucose is required, and therefore the demand for devices related to blood glucose measurement is steadily increasing. It has been confirmed through various studies that the occurrence of complications of diabetes is significantly reduced when diabetic patients strictly control blood glucose. Accordingly, it is very important for diabetics to regularly measure blood glucose in order to manage blood glucose.

In general, a finger prick method is mainly used for blood glucose management by diabetic patients and this type of blood sugar collection system helps the diabetic patients in managing their blood glucose, but it is difficult to accurately identify the blood glucose levels which are being frequently changed because it shows only the result at the time of the measurement. In addition, the finger prick type blood glucose device needs to collect blood several times from time to time even in a day, so diabetics have a burden on blood collection.

Diabetics patients generally experience hyperglycemia and hypoglycemia, and an emergency may occur in the hypoglycemic conditions. The patients may become unconscious or die if a hypoglycemic condition lasts for an extended period of time without the supply of sugar. Accordingly, rapid discovery of the hypoglycemic condition is critically important for diabetics. However, blood-collecting type glucose monitoring devices intermittently measuring glucose have limited ability to accurately measure blood glucose levels.

To overcome such a drawback, continuous glucose monitoring systems (CGMSs) inserted into the human body to measure a blood glucose level every few minutes have been developed, and therefore easily perform the management of diabetics and responses to an emergency situation.

A continuous blood glucose monitoring system comprises a sensor transmitter attached to human body of a user, extracting body fluid, and measuring blood glucose, and a communication terminal displaying a received blood glucose level. The sensor transmitter generates blood glucose information by measuring the blood glucose of the user for a certain period, for example, around fifteen (15) days, in a state that the sensor transmitter is inserted into the human body. The sensor transmitter periodically generates the blood glucose information, and the communication terminal periodically receives the blood glucose information and outputs the received blood glucose information so that the user can check the blood glucose information.

In the continuous blood glucose monitoring system described above, the sensor transmitter and the communication terminal transmit and receive the blood glucose information in a wired way or a wireless way, and the communication terminal requires to continuously receive transmission packets without loss from the sensor transmitter.

However, sometimes, the communication terminal cannot continuously receive the blood glucose information from the sensor transmitter due to temporary communication disconnection between the sensor transmitter and the communication terminal, and therefore, the user cannot continuously monitor his or her blood glucose information through the communication terminal.

DETAILED DESCRIPTION OF DISCLOSURE

Technical Problem

To solve the problem of the conventional method of transmitting and receiving biometric information between a sensor transmitter and a communication terminal, the purpose of the present disclosure may be for providing a method for transmitting and receiving biometric information in a continuous blood glucose monitoring system in which, by generating a transmission packet so as to include a generation identifier for identifying biometric information or the transmission packet according to a generation order of the biometric information or the transmission packet when generating the transmission packet, the biometric information can be transmitted and received without loss through the generation identifier.

Another purpose of the present disclosure may be for providing a method in which, by precisely determining one or more transmission packets or biometric information not received by a communication terminal based on a packet generation identifier or a total number of transmission packets, only the transmission packets or biometric information not received between a sensor transmitter and the communication terminal can be found and transmitted and received.

Still another purpose of the present disclosure may be for providing a method which can transmit and receive biometric information without loss, even though a sensor transmitter does not transmit a transmission completion message after the completion of the transmission of a transmission packet or a communication terminal does not transmit a receipt completion message after the completion of the receipt of the transmission packet.

Solution to Problem

In order to accomplish the purpose of the present disclosure, according to an embodiment of the present disclosure, a method of transmitting and receiving biometric information between a sensor transmitter configured to be attachable to a body part of a user and measure the biometric information of the user and a communication terminal configured to receive the biometric information from the sensor transmitter, the method may comprise, by the sensor transmitter, generating transmission packets including the biometric information measured by a monitor sensor and transmit the transmission packets including the biometric information to the communication terminal, wherein each of the transmission packets comprises a generation identifier which identifies the biometric information or each of the transmission packets according to a generation sequential order of the biometric information or each of the transmission packets.

In this embodiment, each of the transmission packets comprises a plurality of pieces of the biometric information measured at a predetermined measurement time interval, and a distinct packet generation identifier is assigned to a respective single transmission packet comprising the plurality of pieces of the biometric information.

In this embedment, a distinct biometric information generation identifier is assigned to the plurality of pieces of the biometric information included in each of the transmission packets.

In a method of transmitting and receiving biometric information, the sensor transmitter increments a biometric information count when the biometric information is generated at the predetermined measurement time interval, and stores a total number of the biometric information generated by the sensor transmitter based on the biometric information count, or the sensor transmitter increments a transmission packet count when each of the transmission packets comprising the plurality of pieces of the biometric information sequentially generated is generated, and stores a total number of the transmission packets generated by the sensor transmitter based on the transmission packet count.

Preferably, a method of transmitting and receiving biometric information comprises: transmitting, from the communication terminal to the sensor transmitter, an information request message requesting transmission data information; in response to the information request message, transmitting, from the sensor transmitter to the communication terminal, the transmission data information; and based on the transmission data information, requesting, by the communication terminal, the sensor transmitter to transmit a transmission packet or biometric information corresponding to a transmission packet generation identifier or biometric information generation identifier which the communication terminal does not receive.

In this embodiment, the transmission data information comprises a transmission packet generation identifier of a transmission packet latest generated by the sensor transmitter or a biometric information generation identifier of biometric information latest generated by the sensor transmitter.

In this embodiment, the transmission data information comprises the total number of the transmission packets or the total number of the biometric information counted by the sensor transmitter.

Preferably, according to an embodiment of the present disclosure, the requesting the sensor transmitter to transmit the transmission packet or biometric information comprises: comparing the total number of the transmission packets received from the sensor transmitter with a total number of transmission packets registered to the communication terminal; if the total number of the transmission packets received from the sensor transmitter is different from the total number of the transmission packets registered to the communication terminal, compare the transmission packet generation identifier of the transmission packet latest generated by the sensor transmitter with a transmission packet generation identifier of a transmission packet latest received by the communication terminal; if the transmission packet generation identifier of the transmission packet latest generated by the sensor transmitter and the transmission packet generation identifier of the transmission packet latest received by the communication terminal are different from each other, request one or more transmission packets sequentially generated corresponding to from a transmission packet generation identifier next to the transmission packet generation identifier of the transmission packet latest received by the communication terminal to the transmission packet generation identifier of the transmission packet latest generated by the sensor transmitter; and receiving the requested one or more transmission packets from the sensor transmitter.

Preferably, according to another embodiment of the present disclosure, the requesting the sensor transmitter to transmit the transmission packet or biometric information comprises: comparing the total number of the biometric information received from the sensor transmitter with a total number of biometric information registered to the communication terminal; if the total number of the biometric information received from the sensor transmitter is different from the total number of the biometric information registered to the communication terminal, compare the biometric information generation identifier of the biometric information latest generated by the sensor transmitter with a biometric information generation identifier of biometric information latest received by the communication terminal; if the biometric information generation identifier of the biometric information latest generated by the sensor transmitter and the biometric information generation identifier of the biometric information latest received by the communication terminal are different from each other, request one or more biometric information sequentially generated corresponding to from a biometric information generation identifier next to the biometric information generation identifier of the biometric information latest received by the communication terminal to the biometric information generation identifier of the biometric information latest generated by the sensor transmitter; and receiving a transmission packet comprising the requested one or more biometric information from the sensor transmitter.

Preferably, according to still another embodiment of the present disclosure, the requesting the sensor transmitter to transmit the transmission packet or biometric information further comprises: finding at least one transmission packet comprising the one or more biometric information sequentially generated corresponding to from the biometric information generation identifier next to the biometric information generation identifier of the biometric information latest received by the communication terminal to the biometric information generation identifier of the biometric information latest generated by the sensor transmitter; and sequentially receiving the found at least one transmission packet from the sensor transmitter.

According to an embodiment of the present disclosure, a method of transmitting and receiving biometric information comprises: after transmission of the transmission packets, the sensor transmitter does not transmit a packet transmission completion message to the communication terminal; and after receipt of the transmission packets, the communication terminal does not transmit a receipt completion message to the sensor transmitter.

Advantageous Effects of Invention

A method for transmitting and receiving biometric information according to the present disclosure may have various advantageous technical effect as follows.

Firstly, a method for transmitting and receiving biometric information according to the present disclosure, by generating a transmission packet so as to include a generation identifier for identifying biometric information or the transmission packet according to a generation order of the biometric information or the transmission packet when generating the transmission packet, can transmit and receive the biometric information without loss through the generation identifier.

Secondly, a method for transmitting and receiving biometric information according to the present disclosure, by precisely determining one or more transmission packets or biometric information not received by a communication terminal based on a packet generation identifier or a total number of transmission packets, can find and transmit and receive only the transmission packets or biometric information not received between a sensor transmitter and the communication terminal.

Thirdly, a method for transmitting and receiving biometric information according to the present disclosure can transmit and receive biometric information without loss without a separate additional process for confirming transmission completion or receipt completion of the transmission packet, even though a sensor transmitter does not transmit a transmission completion message after the completion of the transmission of a transmission packet or a communication terminal does not transmit a receipt completion message after the completion of the receipt of the transmission packet.

BRIEF DESCRIPTION OF THE DRAWINGS

FIG. 1 is a schematic diagram for illustrating a continuous blood glucose measurement system according to an embodiment of the present disclosure.

FIG. 2 is a figure illustrating an applicator for attaching a sensor transmitter to a human body according to an embodiment of the present disclosure.

FIGS. 3 and 4 are figures for illustrating a process of attaching a sensor transmitter to a human body using an applicator according to an embodiment of the present disclosure.

FIG. 5 is a figure for illustrating messages transmitted and received between a sensor transmitter and a communication terminal.

FIG. 6 is a block diagram for illustrating a sensor transmitter according to an embodiment of the present disclosure.

FIG. 7 is a figure for illustrating an exemplary embodiment of generating a transmission packet by a sensor transmitter.

FIG. 8 is a block diagram for illustrating a communication terminal according to an embodiment of the present disclosure.

FIG. 9 is a flow chart for illustrating a method for receiving a transmission packet not received from a sensor transmitter according to an embodiment of the present disclosure.

FIG. 10 illustrates examples of user interface displays activated on a communication terminal when unreceived transmission packet exists.

FIG. 11 is a flowchart for illustrating a method for receiving one or more unreceived transmission packets by a communication terminal according to an embodiment of the present disclosure.

FIG. 12 is a figure for illustrating an area to which biometric information of an unreceived transmission packet belongs.

FIG. 13 is a flow chart for illustrating a method of determining whether an unreceived transmission packet exists according to an embodiment of the present disclosure.

FIG. 14 is a flowchart for illustrating a method of determining whether one or more unreceived transmission packets exist according to another embodiment of the present disclosure.

DESCRIPTION OF EMBODIMENTS OF DISCLOSURE

The technical terms used in the present disclosure are only for the purpose of describing exemplary embodiments, and they are not intended to limit the present invention. Also, unless otherwise defined, all technical terms used herein should be construed as having the same meaning as commonly understood by those skilled in the art, and should not be interpreted as being excessively inclusive or excessively restrictive. In addition, when a technical term used herein is an erroneous technical term that does not accurately represent the idea of the present invention, it should be understood as replacing the term by a technical term which can be properly understood by those skilled in the art.

Further, singular expressions used in the present specification include plural expressions unless they have definitely opposite meanings. In the present application, it shall not be construed that terms, such as "including" or "comprising", various constituent elements or steps described in the specification need to be all essentially included, and it shall be construed that some constituent elements or steps among the various constituent elements or steps may be omitted, or additional constituent elements or steps may be further included.

Also, it should be noted that the accompanying drawings are merely illustrated to easily explain the spirit of the invention, and therefore, they should not be construed to limit the spirit of the invention by the accompanying drawings.

Hereinafter, with reference to the enclosed drawings, a method for transmitting and receiving biometric information according to an embodiment of the present disclosure is described in detail.

FIG. 1 is a schematic diagram for illustrating a continuous blood glucose measurement system according to an embodiment of the present disclosure.

Referring to FIG. 1, the continuous blood glucose measurement system (1) according to an embodiment of the present disclosure comprises a sensor transmitter (10) and a communication terminal (30).

The sensor transmitter (10) is attachable to human body and, when the sensor transmitter (10) is attached to the human body, an end portion of a sensor of the sensor transmitter (10) is inserted into skin to periodically extract body fluid of the human body and measure blood glucose.

The communication terminal (30) is a terminal configured to receive blood glucose information from the sensor transmitter (10) and output or display the received blood glucose information to a user, and for example, the communication terminal (30) may be a portable terminal (such as smartphone, tablet PC, or notebook and so on) configured to communicatable with the sensor transmitter (10). However, the communication terminal (30) is not limited thereto, and may be any type of a terminal which has a communication function and program or application can be installed to.

The sensor transmitter (10) transmits the blood glucose information in response to request of the communication terminal (30) or at predetermined times periodically, and for data communication between the sensor transmitter (10) and the communication terminal (30), the sensor transmitter (10) and the communication terminal (30) are communicationally connected to each other over a wire by an USB cable and so on or communicationally connected in an wireless communication means such as infrared communication, NFC communication, Bluetooth, etc.

The sensor transmitter (10) is attached to a part of the human body by an applicator, FIG. 2 is a figure illustrating an applicator for attaching a sensor transmitter to a part of a human body according to an embodiment of the present disclosure, and FIGS. 3 and 4 are figures for illustrating a process of attaching a sensor transmitter to a human body using an applicator according to an embodiment of the present disclosure.

Firstly, an application (50) is now described by referring to FIG. 2, the sensor transmitter (10) is mounted in the applicator (50), and the applicator (50) can be operated so that the sensor transmitter (10) can be outwardly discharged to the outside of the applicator (50) by the manipulation of the user and then be attached to a specific portion of the human body of the user. The applicator (50) is formed to have a shape that one side of the applicator (50) is open, and the sensor transmitter (10) is installed to the applicator (50) through the open side of the applicator (50).

When the sensor transmitter (10) is attached to a part of the human body using the applicator (50), for inserting an end portion of the sensor included in the sensor transmitter (10) to skin, the applicator (50) comprises a needle (not shown) formed to cover the end portion of the sensor therein, a first elastic means (not shown) pushing the needle and the end portion of the sensor together towards the skin, and a second elastic means (not shown) configured to retract the needle only. The compressed state of the first elastic means (not shown) arranged to be compressed inside the applicator (50) by the configuration of the applicator (50) can be released, thereby inserting the needle and the end portion of the sensor simultaneously to the skin, and when the end portion of the sensor is inserted to the skin, the compressed state of the second elastic means (not shown) is released, thereby extracting the needle only. By the applicator (50), the user can safely and easily attach the sensor transmitter (10) to the skin.

A process of attaching the sensor transmitter (10) to the human body will be described in detail with reference to FIGS. 3 and 4, in a state that a protection cap (51) is separated or removed, an open side of the applicator (50) is closely placed on a specific part of skin (20) of the human body. When the applicator (50) is operated in a state that the applicator (50) is closely placed on the skin (20) of the human body, the sensor transmitter (10) is outwardly discharged from the applicator (50) and then attached to the skin (20). Here, an end portion of the sensor (12) is arranged to be exposed from the sensor transmitter (10) at a lower portion of the sensor transmitter (10), and a part of the end portion of the sensor (12) is inserted into the skin (20) by a needle installed at the applicator (50). Accordingly, the sensor transmitter (10) can be attached to the skin (20) in a state that an end portion of the sensor (12) is inserted to the skin (20).

In the embodiment of the present disclosure, an adhesive tape is provided at a surface of the sensor transmitter (10) contacting the human body so that the sensor transmitter (10) can be attached to the skin (20). Accordingly, if the applicator (50) is moved away from the skin (20) of the human body, the sensor transmitter (10) is fixedly attached to the skin (20) of the human body by the adhesive tape.

After that, if the power is supplied to the sensor transmitter (10), the sensor transmitter (10) is communicationally connected with the communication terminal (50), and the sensor transmitter (10) transmits the measured blood glucose information to the communication terminal (30).

The sensor transmitter (10) can measure not only the blood glucose information but also various biometric information, and hereinafter blood glucose information is illustrated as one of examples of biometric information.

FIG. 5 is a figure for illustrating messages transmitted and received between a sensor transmitter and a communication terminal.

Referring to FIG. 5, a communication for transmitting and receiving data between the sensor transmitter and the communication terminal is connected (S1). The sensor transmitter and the communication terminal are connected via wire such as the USB cable and so on or via a wireless communication means, for example, infrared communication, NFC communication, Bluetooth, etc, but their detailed descriptions are omitted herein.

When the communication between the sensor transmitter and the communication terminal is connected, the sensor transmitter transmits to the communication terminal transmission packets generated at a predetermined first cycle or in response to a request from the communication terminal (S3).

It may happen that a transmission packet is incapable of being temporarily transmitted due to communication disconnection and the like even though the communication terminal and the sensor transmitter are connected for a certain time period only or continuously, and therefore, the communication terminal transmits a information request message for sequentially receiving transmission packets from the sensor transmitter or receiving one or more transmission packets which have not received among transmission packets generated by the sensor transmitter (S5).

Depending on fields to which the present disclosure is applied, the information request message may be transmitted every time when receipt requests are transmitted or at predetermined times or cycles periodically. The information request message may be transmitted every one (1) hour, every twelve (12) hours, every day periodically and whether an unreceived transmission packet exists may be determined, preferably, the information request message is synchronized to time for storing biometric information by the sensor transmitter and is periodically transmitted every time the biometric information is stored.

For example, if the sensor transmitter is configured to store transmission packets for twelve (12) hours to internal memory, information request messages may be transmitted every twelve (12) hour which is a storage time of a transmission packet, thereby receiving unreceived transmission packets before the transmission packet is deleted from the sensor transmitter. However, the transmission cycle of information request messages may be set as being shorter than twelve (12) hour which is a storage time of a transmission packet. By setting the transmission cycle of information request messages as described above, the consumption of the power for checking and receiving unreceived transmission packets may be reduced and the process overload may be prevented.

Referring back to FIG. 5, in response to the information request message, the sensor transmitter transmits, to the communication terminal, transmission data information comprising information regarding the total number of transmission packets or the total number of biometric information generated by the sensor transmitter as well as a packet generation identifier of a transmission packet most recently generated by the sensor transmitter or a biometric information generation identifier of biometric information most recently generated (S7).

The communication terminal determines whether transmission packets or biometric information which the communication terminal has unreceived exist, and, if there is any transmission packet or biometric information which the communication terminal has not received, the communication terminal transmits, to the sensor transmitter, a transmission packet request message for requesting to transmit one or more transmission packets which have generated by the sensor transmitter after the latest transmission packet or latest biometric information most recently received by the communication terminal (S8).

The sensor transmitter continuously transmits, to the communication terminal, one or more transmission packets including biometric information not received by the communication terminal in response to the transmission packet request message (S9).

As described above by referring to FIG. 5, the method for transmitting and receiving biometric information according to the present disclosure may check whether an unreceived transmission packet or biometric information exists based on the packet generation identifier of the transmission packet or the biometric information generation identifier of the biometric information, and by transmitting and receiving the unreceived biometric information based on this, the loss of the biometric information can be prevented.

Further, by checking the unreceived transmission packet or biometric information based on the packet generation identifier of the transmission packet or the biometric information generation identifier of the biometric information, the sensor transmitter does not need to transmit a packet transmission complete message to the communication terminal after the transmission of the transmission packet, or the communication terminal does not need to transmit a receipt complete message to the sensor transmitter after the receipt of the transmission packet, and therefore the number of the messages transmitted and received for transmission and receipt of the biometric information can be reduced.

FIG. 6 is a block diagram for illustrating a sensor transmitter according to an embodiment of the present disclosure.

The detailed descriptions are provided as follows by referring to FIG. 6, a sensor module (110) includes a sensor, and a part of the sensor is inserted into the human body and the sensor measures blood glucose information.

A sensor control unit or controller (130) receives the blood glucose information measured from the sensor module (110) and stores the received blood glucose information to a storage unit (150). Here, the blood glucose information received from the sensor module (110) by the sensor controller (130) may be an analog signal, and the sensor controller (130) removes noise from the analog signal and transforms it to a digital signal to generate blood glucose information.

The sensor controller (130) increments a count when blood glucose information is generated, and stores the total number of the blood glucose information to the storage unit (150). Meanwhile, the sensor controller (130) controls a transmission packet generation unit (170) so that, when the number of the generated blood glucose information counted by the sensor controller (130) reaches a predetermined number of blood glucose information, one or more transmission packets are generated from the plurality of blood glucose information.

According to the control of the sensor controller (130), the transmission packet generation unit (170) generates a transmission packet consisting of sequential blood glucose information for a certain time period by combining blood glucose information which is sequentially stored in a time order to the storage unit (150). Here, the transmission packet generation unit (170) generates the transmission packet by adding a generation identifier for identifying each blood glucose information, comprised in the transmission packet, to the transmission package.

The sensor controller (130) increments a count when the transmission packet is generated by the transmission packet generation unit (170), and stores the total number of the transmission packets to the storage unit (150). The sensor controller (130) transmits the stored transmission packets through a sensor communication unit (190) to the communication terminal at a predetermined transmission cycle or in response to a request of the communication terminal.

Meanwhile, the sensor controller (130) provides information on the total number of the generated transmission packets or the total number of the generated biometric information, or provides a generation identifier of the latest transmission packet most recently generated or a generation identifier of the latest biometric information most recently generated, and when the communication terminal requests a transmission packet or biometric information which the communication terminal has not received, the sensor controller (130) controls to extract the unreceived transmission packet or biometric information from the storage unit (150) based on the generation identifier of the unreceived transmission packet or the generation identifier of the unreceived biometric information and to transmit the extracted transmission packet or packet information to communication terminal.

FIG. 7 is a figure for illustrating an exemplary embodiment of generating a transmission packet by a sensor transmitter, as illustrated in FIG. 7, a transmission packet (P) is generated from five (5) pieces of biometric information (v) sequentially generated for a set time period (T), and when biometric information is generated at a constant time interval for the set time period (T), the number of the generated blood glucose information is counted, for example, when five (5) pieces of the blood glucose information are generated, a transmission packet is generated from the five (5) pieces of the blood glucose information. The transmission packet generation unit (170) assigns a generation identifier for identifying each blood glucose information when the blood glucose information is generated, or assigns a generation identifier for identifying each transmission packet when the transmission packet is generated. Here, the generation identifier is unique, and, preferably, the transmission packet generation unit (170) can assign sequence, which is sequentially increased according to a generation order of the blood glucose information or a generation order of the transmission packet, as a generation identifier, or can assign generation time of the blood glucose information or generation time of the transmission packet as a generation identifier.

FIG. 8 is a block diagram for illustrating a communication terminal according to an embodiment of the present disclosure.

Referring to FIG. 8, a terminal controller (210) performs communication with sensor transmitter through a terminal communication unit (230) at every set first cycle or for requesting biometric information.

The terminal controller (210) receives a transmission packet including a plurality of biometric information from the sensor transmitter, and stores the received transmission packet to a storage unit (250). The terminal controller (210) controls to output biometric information of the received transmission packet on a display unit (270) so that a user can check the biometric information of the received transmission packet. Meanwhile, every time when the terminal controller (210) receives a transmission packet, the terminal controller (210) increments count and registers and stores a total number of the transmission packets, which the communication terminal receives from the sensor transmitter, to the storage unit (250), or every time when the terminal controller (210) receives a transmission packet, the terminal controller (210) increments count according to the number of biometric information included in the transmission packet and registers and stores a total number of the biometric information, which the communication terminal receives from the sensor transmitter, to the storage unit (250).

The terminal controller (210) receives transmission data information from the sensor transmitter for continuously receiving a transmission packet from the sensor transmitter or checking whether a transmission packet not received by the communication terminal exists, and continuously requests a transmission packet based on the received transmission data information or requests transmission of an unreceived transmission packet. Here, the transmission data information includes a packet generation identifier of a latest transmission packet most recently generated by the sensor transmitter or a biometric information generation identifier of a latest biometric information most recently generated by the sensor transmitter, or a total number of transmission packets or a total number of biometric information counted by the sensor transmitter.

For continuously receiving transmission packets from the sensor transmitter or receiving unreceived transmission packets from the sensor transmitter, the terminal controller (210) compares a total number of transmission packets received from the sensor transmitter and a total number of transmission packets registered to the communication terminal, and requests transmission of one or more transmission packets or biometric information generated by the sensor transmitter after the packet generation identifier of the latest transmission packet or the biometric information generation identifier of the latest biometric information most recently received by the communication terminal based on the comparison result.

Preferably, when a transmission packet or biometric information unreceived from the sensor transmitter, the terminal controller (210) controls to output an indication that the unreceived transmission packet or biometric information exists on the display unit (270), and when a receipt request command of the unreceived transmission packet or biometric information is inputted through an user interface unit (290), the terminal controller (210) requests the unreceived transmission packet or biometric information from the sensor transmitter.

Additionally, the terminal controller (210) can control to selectively receive the unreceived transmission packet based on whether an area to which biometric information of the unreceived transmission packet belongs is a dangerous area or a non-dangerous area.

FIG. 9 is a flow chart for illustrating a method for receiving a transmission packet not received from a sensor transmitter according to an embodiment of the present disclosure.

Referring to FIG. 9, the communication terminal receives a information request message for requesting transmission data information to sensor transmitter (S110).

In response to the information request message, the communication terminal receives, from the sensor transmitter, transmission data information comprising information on a total number of transmission packets or a total number of biometric information generated by the sensor transmitter and a packet generation identifier of the latest transmission packet most recently generated or a biometric information generation identifier of the latest biometric information most recently generated (S130).

The communication terminal determines whether there is a transmission packet not received by the communication terminal by comparing a total number of transmission packets or a total number of biometric information registered and stored to the communication terminal with a total number of transmission packets or a total number of biometric information included in the transmission data information or comparing a packet generation identifier of the latest transmission packet or a biometric information generation identifier of the latest biometric information registered and stored to the communication terminal with a packet generation identifier of the latest transmission packet or a biometric information generation identifier of the latest biometric information included in the transmission data information (S150).

When the unreceived transmission packet exists, the communication terminal requests the sensor transmitter to transmit one or more unreceived transmission packets after the packet generation identifier of the latest transmission packet or the biometric information generation identifier of the latest biometric information most recently received by the communication terminal, and receives the unreceived transmission packets (S190).

Preferably, when a transmission packet not received by the communication terminal exists, the unreceived transmission packet can be received without asking to the user, but the user can be notified regarding the existence of the unreceived transmission packet, whether a user command for requesting the receipt of the unreceived transmission packet is inputted through a user interface unit is determined, and the unreceived transmission packet can be received depending on the user's selection (S170). This is for selectively receiving the unreceived transmission packet according to the determination of the user in order to reduce power consumption for receiving unnecessary past biometric information or prevent process overload.

FIG. 10 illustrates examples of user interface displays activated on a communication terminal when unreceived transmission packet exists.

As illustrated in FIG. 10(a), a display unit of the communication terminal displays biometric information of a user as a graph on a time axis (t), and when the unreceived transmission packet exists, an icon (X) is activated in order to notify existence of the unreceived transmission packet to the user, and the user can select the icon to check the unreceived transmission packet in consideration of time of the unreceived biometric information.

As illustrated in FIG. 10(b), if the user selects the icon, the user is notified that there are five (5) unreceived transmission packets by comparing a total number of transmission packets registered and stored to the communication terminal and a total number of transmission packets included in the receipt data information and determining the number of the unreceived transmission packets. The user can input a user command for receiving the unreceived transmission packet through a receipt icon.

As illustrated in FIG. 10(c), when the user command for receiving the five (5) unreceived transmission packets is inputted, the communication terminal receives the unreceived transmission packets from the sensor transmitter, and activates an icon for checking biometric information of the received transmission packets.

FIG. 11 is a flowchart for illustrating a method for receiving one or more unreceived transmission packets by a communication terminal according to an embodiment of the present disclosure.

Referring to FIG. 11, whether one or more transmission packets not received from the sensor transmitter exist is determine (S211).

When the unreceived transmission packet exists, a terminal controller determines an area to which the biometric information included in the unreceived transmission packet belongs by determining that the biometric information included in the unreceived transmission packet is within a dangerous area or within an undangerous area (S213). When the biometric information included in the unreceived transmission packet is within the dangerous area, the transmission of the unreceived transmission packet from the sensor transmitter (10) is requested without a receipt request of the user (S217).

However, if the biometric information included in the unreceived transmission packet is within the undangerous area, whether the receipt request is inputted from the user is determined (S219). Only if the receipt request of the user is inputted, the transmission of the unreceived transmission packet from the sensor transmitter is requested.

FIG. 12 is a figure for illustrating an area to which biometric information of an unreceived transmission packet belongs, as illustrated in FIG. 12(a), biometric information generated by a sensor transmitter is continuous blood glucose information of a user with respect to time change, and this biometric information is changed according to time. When a blood glucose level of the user based on the biometric information is equal to or less than a first threshold value (TH1), it is in a hypoglycemia dangerous area, and when the blood glucose level of the user is equal to or more than a second threshold value (TH2), it is in a hyperglycemia dangerous area.

As illustrated in FIG. 12(b), a transmission packet not received from the sensor transmitter exists and, based on a time period (t1) of the unreceived transmission packet, it is predicted that the biometric information of the unreceived transmission packet is in the hyperglycemia dangerous area which is higher than the second threshold value (TH2) from adjacent biometric information which is adjacent to the biometric information of the unreceived transmission packet.

However, as illustrated in FIG. 12(c), a transmission packet not received from the sensor transmitter exists and, based on a time period (t2) of the unreceived transmission packet, it is predicted that the biometric information of the unreceived transmission packet is in the undangerous area which is between the first threshold value (TH1) and the second threshold value (TH2) from adjacent biometric information which is adjacent to the biometric information of the unreceived transmission packet.

Preferably, based on an area to which the biometric information of time adjacent to the unreceived transmission packet belong, an area to which the biometric information of the unreceived transmission packet belongs is determined, or by considering a blood glucose value, a slope, and speed change of the biometric information of time adjacent to the unreceived transmission packet and so on, an area to which the biometric information of the unreceived transmission packet belongs is determined.

FIG. 13 is a flow chart for illustrating a method of determining whether an unreceived transmission packet exists according to an embodiment of the present disclosure.

Referring to FIG. 13, by comparing a total number of transmission packets included in the transmission data information received from the sensor transmitter with a total number of transmission packets registered to the communication terminal, whether a total number of transmission packets included in the transmission data information received from the sensor transmitter and a total number of transmission packets registered to the communication terminal are identical to each other is determined (S231).

When a total number of transmission packets included in the transmission data information received from the sensor transmitter is different from a total number of transmission packets registered to the communication terminal, comparison between a packet generation identifier of the latest transmission packet most recently generated by the sensor transmitter and a packet generation identifier of the latest transmission packet most recently generated by the communication terminal is performed (S233).

When a packet generation identifier of the latest transmission packet most recently generated by the sensor transmitter is different from a packet generation identifier of the latest transmission packet most recently generated by the communication terminal, one or more packets not received by the communication terminal after the packet generation identifier of the latest transmission packet most recently generated by the communication terminal before the packet generation identifier of the latest transmission packet most recently generated by the communication terminal are determined and found (S235).

By receiving one or more packet generation identifiers of the unreceived transmission packets, the received transmission packets are sequentially received from the sensor transmitter (S237).

FIG. 14 is a flowchart for illustrating a method of determining whether one or more unreceived transmission packets exist according to another embodiment of the present disclosure.

A total number of biometric information included in the transmission data information received from the sensor transmitter and a total number of biometric information registered to the communication terminal are compared to each other (S251). When a total number of biometric information included in the transmission data information received from the sensor transmitter is different from a total number of biometric information registered to the communication terminal, comparison between a biometric information generation identifier of the latest biometric information most recently generated by the sensor transmitter and a biometric information generation identifier of the latest biometric information most recently generated by the communication terminal is performed (S253).

When the biometric information generation identifier of the latest biometric information most recently generated by the sensor transmitter is different from the biometric information generation identifier of the latest biometric information most recently generated by the communication terminal, biometric information not received by the communication terminal after the biometric information generation identifier of the latest biometric information most recently generated by the communication terminal before the biometric information generation identifier of the latest biometric information most recently generated by the communication terminal are determined and found (S255).

A transmission packet including the unreceived biometric information is requested and received from the sensor transmitter (S259).

Preferably, based on one or more biometric information generation identifiers generated between the biometric information generation identifier of the latest biometric information most recently generated by the sensor transmitter and the biometric information generation identifier of the latest biometric information most recently generated by the communication terminal, the communication terminal or the sensor transmitter finds and determines at least one transmission packet including biometric information sequentially generated from the biometric information generation identifier of the latest biometric information most recently generated by the sensor transmitter to the biometric information generation identifier of the latest biometric information most recently generated by the communication terminal (S257). The communication terminal is sequentially received the found unreceived transmission packets from the sensor transmitter.

The embodiments of the present invention may be written as computer programs and may be implemented in general-use digital computers that execute the programs using a computer readable recording medium.

Examples a the computer readable recording medium include magnetic storage media (e.g., ROM, floppy disks, hard disks, etc.), optical recording media (e.g., CD-ROMs, or DVDs) and carrier wave (e.g. transmission through the Internet).

Although the present disclosure is described with exemplary embodiments illustrated in the drawings, the foregoing descriptions have been presented by way of example, and a person having ordinary skill in the art which the present disclosure relates could make various modifications and equivalent other embodiments. Accordingly, it should be understood that the scope of the present disclosure shall be defined by the Claims and all of their equivalents fall within the scope of the present disclosure.

What is claimed is:

1. A method of transmitting and receiving biometric information between a sensor transmitter configured to be attachable to a body part of a user and measure the biometric information of the user and a communication terminal configured to receive the biometric information from the sensor transmitter, the method comprising:

by the sensor transmitter, generating transmission packets including the biometric information measured by a monitor sensor and transmit the transmission packets including the biometric information to the communication terminal;

determining whether one or more transmission packets not received from the sensor transmitter exist;

if the unreceived transmission packet exists, determining an area to which the biometric information included in the unreceived transmission packet belongs by determining that the biometric information included in the unreceived transmission packet is within a dangerous area or within an undangerous area wherein the dangerous area is determined by a first threshold value and a second threshold value;

if the biometric information included in the unreceived transmission packet is within the dangerous area, transmitting, from the communication terminal to the sensor transmitter, an information request message requesting the biometric information, transmitting, from the communication terminal to the sensor transmitter, an information request message requesting transmission data information;

in response to the information request message, transmitting, from the sensor transmitter to the communication terminal, the transmission data information;

based on the transmission data information, requesting, by the communication terminal, the sensor transmitter to transmit a transmission packet or biometric information corresponding to a transmission packet generation identifier or biometric information generation identifier which the communication terminal does not receive, wherein the requesting the sensor transmitter to transmit the transmission packet or biometric information comprises:

comparing the total number of the transmission packets received from the sensor transmitter with a total number of transmission packets registered to the communication terminal;

if the total number of the transmission packets received from the sensor transmitter is different from the total number of the transmission packets registered to the communication terminal, compare the transmission packet generation identifier of the transmission packet latest generated by the sensor transmitter with a transmission packet generation identifier of a transmission packet latest received by the communication terminal;

if the transmission packet generation identifier of the transmission packet latest generated by the sensor transmitter and the transmission packet generation identifier of the transmission packet latest received by the communication terminal are different from each other, request one or more transmission packets sequentially generated which includes transmission packets from transmission packets corresponding to a transmission packet generation identifier which generated sequentially to the transmission packet generation identifier of the transmission packet latest received by the communication terminal to transmission packets corresponding to the transmission packet generation identifier of the transmission packet latest generated by the sensor transmitter; and receiving the requested one or more transmission packets from the sensor transmitter, wherein each of the transmission packets comprises a generation identifier which identifies the biometric information or each of the transmission packets according to a generation sequential order of the biometric information or each of the transmission packets, wherein the transmission data information comprises a transmission packet generation identifier of a transmission packet latest generated by the sensor transmitter or a biometric information generation identifier of biometric information latest generated by the sensor transmitter, wherein the transmission data information comprises the total number of the transmission packets or the total number of the biometric information counted by the sensor transmitter, wherein each of the transmission packets comprises a plurality of pieces of the biometric information measured at a predetermined measurement time interval, and a distinct packet generation identifier is assigned to a respective single transmission packet comprising the plurality of pieces of the biometric information, wherein a distinct biometric information generation identifier is assigned to the plurality of pieces of the biometric information included in each of the transmission packets, wherein the sensor transmitter increments a biometric information count when the biometric information is generated at the predetermined measurement time interval, and stores a total number of the biometric information generated by the sensor transmitter based on the biometric information count, or the sensor transmitter increments a transmission packet count when each of the transmission packets comprising the plurality of pieces of the biometric information sequentially generated is generated, and stores a total number of the transmission packets generated by the sensor transmitter based on the transmission packet count.

2. The method of claim 1 transmitting and receiving the biometric information, wherein:

after transmission of the transmission packets, the sensor transmitter does not transmit a packet transmission completion message to the communication terminal; and after receipt of the transmission packets, the communication terminal does not transmit a receipt completion message to the sensor transmitter.

3. A method of transmitting and receiving biometric information between a sensor transmitter configured to be attachable to a body part of a user and measure the biometric information of the user and a communication terminal configured to receive the biometric information from the sensor transmitter, the method comprising:

by the sensor transmitter, generating transmission packets including the biometric information measured by a monitor sensor and transmit the transmission packets including the biometric information to the communication terminal;

determining whether one or more transmission packets not received from the sensor transmitter exist;

if the unreceived transmission packet exists, determining an area to which the biometric information included in the unreceived transmission packet belongs by determining that the biometric information included in the unreceived transmission packet is within a dangerous area or within an undangerous area wherein the dangerous area is determined by a first threshold value and a second threshold value;

if the biometric information included in the unreceived transmission packet is within the dangerous area, transmitting, from the communication terminal to the sensor transmitter, an information request message requesting the biometric information, transmitting, from the communication terminal to the sensor transmitter, an information request message requesting transmission data information;

in response to the information request message, transmitting, from the sensor transmitter to the communication terminal, the transmission data information;

based on the transmission data information, requesting, by the communication terminal, the sensor transmitter to transmit a transmission packet or biometric information corresponding to a transmission packet generation identifier or biometric information generation identifier which the communication terminal does not receive, wherein the requesting the sensor transmitter to transmit the transmission packet or biometric information comprises;

comparing the total number of the biometric information received from the sensor transmitter with a total number of biometric information registered to the communication terminal;

if the total number of the biometric information received from the sensor transmitter is different from the total number of the biometric information registered to the communication terminal, compare the biometric information generation identifier of the biometric information latest generated by the sensor transmitter with a biometric information generation identifier of biometric information latest received by the communication terminal;

if the biometric information generation identifier of the biometric information latest generated by the sensor transmitter and the biometric information generation identifier of the biometric information latest received by the communication terminal are different from each other, request one or more biometric information sequentially generated which includes transmission packets from transmission packets corresponding to a biometric information generation identifier which generated sequentially to the biometric information generation identifier of the biometric information latest received by the communication terminal to transmission packets corresponding to the biometric information generation identifier of the biometric information latest generated by the sensor transmitter; and receiving a transmission packet comprising the requested one or more biometric information from the sensor transmitter, wherein each of the transmission packets comprises a generation identifier which identifies the biometric information or each of the transmission packets according to a generation sequential order of the biometric information or each of the transmission packets, wherein the transmission data information comprises a transmission packet generation identifier of a transmission packet latest generated by the sensor transmitter or a biometric information generation identifier of biometric information latest generated by the sensor transmitter, wherein the transmission data information comprises the total number of the transmission packets or the total number of the biometric information counted by the sensor transmitter, wherein each of the transmission packets comprises a plurality of pieces of the biometric information measured at a predetermined measurement time interval, and a distinct packet generation identifier is assigned to a respective single transmission packet comprising the plurality of pieces of the biometric information, wherein a distinct biometric information generation identifier is assigned to the plurality of pieces of the biometric information included in each of the transmission packets, wherein the sensor transmitter increments a biometric information count when the biometric information is generated at the predetermined measurement time interval, and stores a total number of the biometric information generated by the sensor transmitter based on the biometric information count, or the sensor transmitter increments a transmission packet count when each of the transmission packets comprising the plurality of pieces of the biometric information sequentially generated is generated, and stores a total number of the transmission packets generated by the sensor transmitter based on the transmission packet count.

4. The method of claim 3 transmitting and receiving the biometric information, wherein the requesting the sensor transmitter to transmit the transmission packet or biometric information further comprises:

finding at least one transmission packet comprising the one or more biometric information sequentially generated corresponding to from the biometric information generation identifier next to the biometric information generation identifier of the biometric information latest received by the communication terminal to the biometric information generation identifier of the biometric information latest generated by the sensor transmitter; and sequentially receiving the found at least one transmission packet from the sensor transmitter.

* * * * *